United States Patent [19]

Giordano et al.

[11] Patent Number: 4,501,913

[45] Date of Patent: Feb. 26, 1985

[54] PROCESS FOR PREPARING ESTERS OF ARYL ALKANOIC ACIDS

[75] Inventors: Claudio Giordano, Vicenza; Graziano Castaldi, Briona, both of Italy

[73] Assignee: Zambon S.p.A., Vicenza, Italy

[21] Appl. No.: 547,632

[22] Filed: Nov. 1, 1983

[30] Foreign Application Priority Data

Nov. 3, 1982 [IT] Italy ................................ 24030 A/82

[51] Int. Cl.³ .............................................. C07G 69/76
[52] U.S. Cl. .................................... 560/100; 560/105;
560/56; 562/466; 562/490; 562/496
[58] Field of Search .......................... 560/56, 100, 105;
562/466, 490, 496

[56] References Cited

U.S. PATENT DOCUMENTS 4,060,690 11/1977 Chahawi et al. ........................ 560/55
4,328,356 5/1982 Giordano et al. ..................... 560/105

FOREIGN PATENT DOCUMENTS 7163337 10/1982 Japan ................................... 560/105

*Primary Examiner*—Paul J. Killos
*Attorney, Agent, or Firm*—Cushman, Darby & Cushman

[57] ABSTRACT

Process for preparing esters of aryl alkanoic acids via oxidation of the corresponding ketones with bromine or iodine in the presence of a metal halide and an alcohol.

The thus obtained esters are then easily hydrolized to give the corresponding aryl alkanoic acids which are particularly useful as anti-inflammatory, analgesic and anti-pyretic agents.

4 Claims, No Drawings

PROCESS FOR PREPARING ESTERS OF ARYL ALKANOIC ACIDS

This invention relates to a new process for preparing esters of aryl alkanoic acids via oxidation of the corresponding ketones with bromine or iodine in the presence of a metal halide and an alcohol.

It is known that many aryl alkanoic acids are used as therapeutic agents because of their anti-inflammatory, analgesic and/or antipyretic activity.

A great number of methods of synthesis has been proposed until now. Many of these methods comprise many steps and therefor they are not very economical.

In order to make simple the method of synthesis, S. D. Higgins et al. (J.Chem. Soc. Perkin I, 235, 1982) proposed a method for converting aryl alkyl ketones into esters of aryl alkanoic acids by oxidation of the first with halogens. Since, however, this method needs the concurrent presence of silver nitrate, the Authors come to the conclusion that it is desirable to find an alternative to the silver nitrate.

Now it has been surprisingly found that the zinc halides may replace advantageously the silver nitrate.

It is therefor an object of this invention a method for preparing aryl alkanoic acids of formula

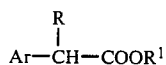

where
A is an aryl radical having from 6 to 15 carbon atoms;
R is an alkyl radical having from 1 to 3 carbon atoms; and
R1 is an alkyl radical having from 1 to 6 carbon atoms or an aryl alkyl radical having from 7 to 12 carbon atoms, by oxidation with bromine or iodine of ketones of formula

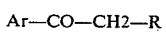

where Ar and R have the above mentioned meanings; in the presence of a zinc halide and of an alcohol of formula R1—OH, where R1 has the above mentioned meaning.

The reaction is preferably carried out by adding the ketone to a mixture in an alcohol (R1OH) of an excess of a zinc halide (from 1.5 to 7 moles for each mole of ketone) and of a small excess of iodine or bromine. The thus obtained mixture is refluxed from some hours; preferably from 1 to 24 hours. The obtained ester is recovered in a conventional way and, if desired, is hydrolized to afford the acid. The thus obtained esters are then easily hydrolized to give the corresponding acids by means of conventional techniques.

Preferred embodiments according to this invention comprise the preparation of ibuprofen (Ar=4-isobutylphenyl; R=methyl) and naproxen (Ar=6-methoxy-2-naphthyl; R=methyl).

The following examples are intended only to illustrate but not to limit this invention.

EXAMPLE 1

Preparation of 2-(6'-methoxy-2'-naphthyl)-propionic acid 1-(6'-methoxy-2'-naphthyl)-propane (2.14 g; 10 mmols) is added to a solution of ZnBr2 (13 g; 57.7 mmols) and iodine (2.66 g; 10.5 mmols) in methanol (7 ml). The mixture is refluxed for 3 hours.

The reaction mixture is then poured into water (150 ml) and extracted with methylene chloride (50 ml×3). The organic extract is washed with water (3×50 ml) and dried over anhydrous sodium sulfate. The solvent is evaporated under vacuum. On the basis of IR, NMR and TLC analysis, the residue is containing the methyl 2-(6'-methoxy-2'-naphthyl)propionate.

The residue is then dissolved into a 30% solution (10 ml) of sodium hydroxide in methanol (30 ml). The mixture is refluxed for two hours, then is diluted with water (100 ml) and extracted with methylene chloride (50 ml×3).

The aqueous layer is made acid with concentrate hydrochloric acid and extracted with methylene chloride (50 ml×3). The organic extract is dried over sodium sulfate.

The evaporation of the solvent under vacuum affords a residue of 2-(6'-methoxy-2'-naphthyl)-propionic acid (1.0 g; 43.5 mmols; Yield, 43.5%) m.p. 154°–155° C.

EXAMPLE 2

Preparation of 4-isobutylphenylpropionic acid 4-isobutylpropiophenone (16.6 g; 0.10 mol) is added to a solution of zinc bromide (130 g; 0.577 mol) and iodine (26.6 g; 0.105 mol) in methanol (70 ml), the mixture is then refluxed for 6 hours. The mixture is poured into water and extracted with methylene chloride. The organic extract is washed with water and dried over sodium sulfate.

The solvent is then evaporated under vacuum and the residue is taken up in 100 ml of 30% sodium hydroxide and 100 ml of methanol.

The mixture is refluxed for two hours, then diluted with water and extracted with methylene chloride. The aqueous phase is made acid with concentrate hydrochloric acid and extracted with methylene chloride.

The organic extract is washed with water and dried with sodium sulfate. The evaporation of the solvent under vacuum affords a residue of 4-isobutylphenylpropionic acid (1.3 g; 0.0063 mol; Yield, 6.3%), m.p. 76°–77° C.

EXAMPLE 3

Preparation of 4-methoxyphenylpropionic acid (a) 4-methoxy-propiophenone (3.28 g; 0.02 mol) is added to a solution of ZnBr2 (26 g; 0.115 mol) and iodine (5.32 g; 0.0205 mol) in methanol (14 ml).

The mixture is heated to the reflux temperature for 6 hours. The mixture is poured into water and extracted with methylene chloride. The organic extract is washed with water, dried over sodium sulfate and the solvent is evaporated in vacuum. The residue is taken up with 10 ml of 30% sodium hydroxide and 10 ml of methanol. The mixture is refluxed for 2 hours, then diluted with water and extracted with methylene chloride.

The aqueous phase is made acid with concentrate hydrochloric acid and extracted with methylene chloride. The organic extract is washed with water and dried over sodium sulfate. The evaporation of the solvent in vacuum affords 4-methoxyphenylpropionic acid (1.23 g; 0.0068 mol; Yield, 34%), m.p. 56°–57° C.

(b) By working according to method (a) but replacing ZnBr2 with 36.6 g (0.115 mol) of ZnI2, it is obtained the 4-methoxypropionic acid; yield, 10%.

(c) By working according to method (a) but replacing ZnBr2 with 15.7 g (0.115 mol) of ZnCl2, it is obtained 4-methoxyphenylpropionic acid; Yield, 16%.

We claim:

1. Process for preparing esters of aryl alkanoic acids of formula

where

Ar is an aryl radical having from 6 to 15 carbon atoms,

R is hydrogen or an alkyl radical having from 1 to 3 carbon atoms,

R1 is an alkyl radical having from 1 to 6 carbon atoms or an aryl alkyl radical having from 7 to 12 carbon atoms, which comprises the oxidation with bromine or iodine of a ketone of formula

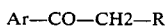

where Ar and R have the above mentioned meanings, in the presence of an alcohol having formula R1—OH, where R1 has the above mentioned meanings, characterized in that the oxidation is carried out in the presence of a zind halide.

2. Process according to claim 1, characterized in that Ar is a radical selected in the group comprising 4-isobutylphenyl and 6-methoxy-2-naphthyl, and R is a methyl radical.

3. Process according to claims 1 and 2, characterized in that it is used at least 1.5 moles of a zinc halide with respect to each mole of ketone.

4. Process according to claims 1 and 2, characterized in that the reaction is carried out at the reflux temperature of the reaction mixture.

* * * * *